United States Patent [19]

Frishberg

[11] 4,324,899
[45] Apr. 13, 1982

[54] 2-AMINO-5-CYANOTHIAZOLES AND THEIR PREPARATION

[75] Inventor: Mark D. Frishberg, Kingsport, Tenn.

[73] Assignee: Eastman Kodak Company, Rochester, N.Y.

[21] Appl. No.: 155,812

[22] Filed: Jun. 2, 1980

Related U.S. Application Data

[63] Continuation-in-part of Ser. No. 55,092, Jul. 5, 1979, abandoned.

[51] Int. Cl.³ .............................................. C07D 277/20
[52] U.S. Cl. ..................................... 548/190; 548/193; 260/158; 546/280; 548/198
[58] Field of Search ............... 548/184, 198, 190, 193; 546/280

[56] References Cited

U.S. PATENT DOCUMENTS 3,113,947 12/1963 Currie ................................. 548/184
4,250,090 2/1981 Eilingsfeld et al. ................. 548/190

Primary Examiner—Nicholas S. Rizzo
Attorney, Agent, or Firm—Donald W. Spurrell; Daniel B. Reece, III

[57] ABSTRACT

Disclosed are novel 2-amino-5-cyanothiazoles and the preparation thereof by a novel, two-step process. The cyanothiazoles have the formula

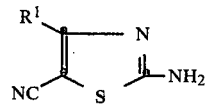

wherein $R^1$ is selected from hydrogen; straight or branched alkyl of 1–20 carbons which may be substituted with 1–3 halogens; phenyl and phenyl substituted with 1–3 halogens, straight or branched alkyl of 1–20 carbons, straight or branched alkoxy of 1–20 carbons, cyano, nitro or trifluoromethyl; 2-thiophene; and α-pyridine. These compounds are useful, for example, as the diazo moiety of azo dyes prepared through diazotization and coupling with compounds such as aniline type couplers. The process for their manufacture comprises reacting in substantially anhydrous formic acid at from about 50° to about 110° C., hydroxylamine, preferably the salts thereof such as [NH₃OH]Cl, [NH₃OH]HSO₄, [NH₃OH]₂SO₄, and [NH₃OH]NO₃, and the corresponding 2-amino-5-formylthiazole or a salt thereof in a mole ratio of said reactants of, for example, from about 1:1 to about 2:1, and hydrolyzing the intermediate 5-cyano-2-formamidothiazole to the amine with or without prior isolation thereof.

9 Claims, No Drawings

2-AMINO-5-CYANOTHIAZOLES AND THEIR PREPARATION

This is a continuation-in-part of application No. 55,092, filed July 5, 1979, now abandoned.

This invention relates to novel 2-amino-5-cyanothiazoles and the preparation thereof by a novel, two-step process. The novel cyanothiazoles have the formula

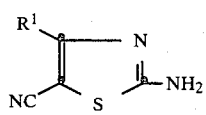

wherein $R^1$ is selected from hydrogen; alkyl of 1-20 carbons which may be substituted with 1-3 halogens; phenyl and phenyl substituted with 1-3 halogens, alkyl of 1-20 carbons, alkoxy of 1-20 carbons, cyano, nitro or trifluoromethyl; 2-thiophene; and α-pyridine, and wherein the various alkyl and alkoxy groups are straight or branched. These compounds are useful, for example, as the diazo moiety of azo dyes prepared through diazotization and coupling with compounds such as aniline, tetrahydroquinoline and benzomorpholine type couplers as disclosed in applicants' copending patent application Ser. No. 17,743.

I have further discovered that the novel 2-amino-5-cyanothiazoles can be obtained by reacting the corresponding 2-amino-5-formylthiazole of the formula below or a hydrohalide salt thereof with hydroxylamine, preferably as a salt such as [NH$_3$OH]Cl, [NH$_3$OH]HSO$_4$, [NH$_3$OH]$_2$SO$_4$, and [NH$_3$OH]NO$_3$ in the presence of formic acid to form the corresponding intermediate 2-formamido-5-cyanothiazole, and then acid hydrolyzing this intermediate in the presence, for example, of a lower alkanol to yield the desired 2-amino-5-cyanothiazole. The term "corresponding" refers to the particular $R^1$ group which the various intermediates and final product carries throughout the present process. The process in preferred form may be depicted as follows:

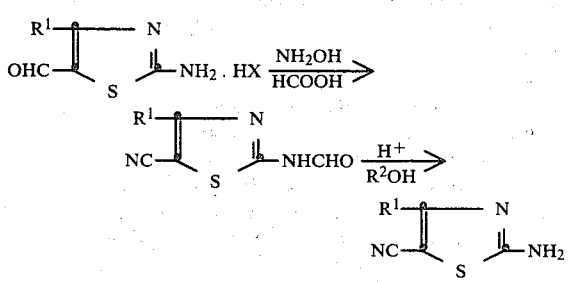

wherein $R^1$ is defined above, $R^2$ may be for example, alkyl of 1-6 carbons or H, the NH$_2$OH is preferably as [NH$_3$OH]Cl or [NH$_3$OH]HSO$_4$, and HX is an acid such as HCl which forms an amine salt. The selective hydrolysis constituting the second step of the process is particularly unique in view of the prior art. For example, in Rec. trav. chim., 66, 226, the same hydrolysis of the homologous 2-acetamido-5-cyanothiazole resulted in the hydrolysis of both the acetamido and cyano groups giving 2-amino-5-ethoxycarbonylthiazole.

The present procedure is of general utility for preparing these types of compounds and is more particularly defined as comprising reacting in formic acid at from about 50° to about 110° C., preferably from about 85° to about 105° C., and for an adequate time, for example, for about 2-16 hrs., preferably for about 5-12 hours, hydroxylamine or the hydrochloride or other salt thereof, and substituted or unsubstituted 2-amino-5-formylthiazole. Any suitable mole ratio can be used, but a mole ratio of from about 1:1 to about 2:1 of the hydroxylamine to the thiazole reactant is preferred, and most preferably from about 1:1 to about 3:2. If desired, from about 1 to 2 moles per mole of hydroxylamine salt of formate salts such as sodium or ammonium formate, or acetate salts may be used as an acid acceptor. The intermediate 5-cyano-2-formamidothiazole is then hydrolyzed to the desired 2-amino compound by known hydrolysis methods and preferably with ethanolic hydrochloric acid. The hydrolysis to the amine may be carried out without isolation of the 5-cyano-2-formamidothiazole by the addition for example of an adequate amount of dilute aqueous or ethanolic hydrochloric acid to the reaction system. In the first step of this process, the amount of water should be kept to a minimum to allow the dehydration reaction to proceed. Typically, commercially available formic acid contains about 3% or so by weight of water.

The above 4-position substituted intermediates may be prepared in known manner according to the following reaction scheme:

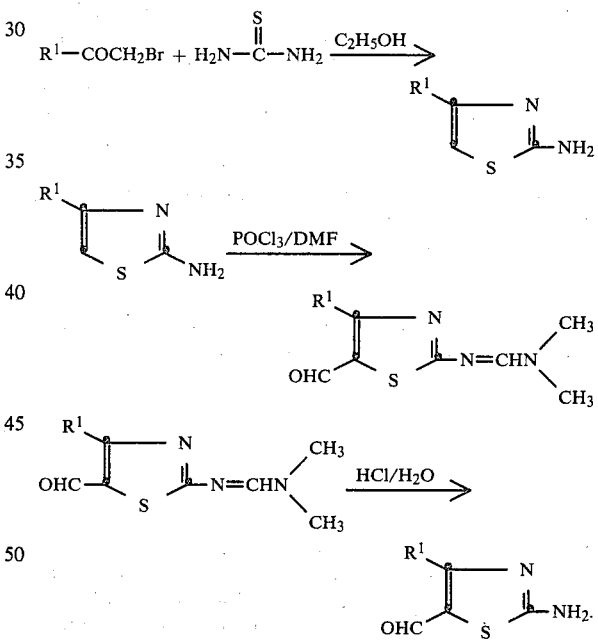

The unsubstituted intermediate may be prepared from bromomalonaldehyde and thiourea as follows:

Bromomalonaldehyde (142 g, 0.94 m) was suspended in 750 ml of water under nitrogen and thiourea (71.5 g, 0.94 m) was added with stirring. A very slight exotherm was noted and a homogeneous yellow solution was obtained in five to ten minutes. After stirring at a temperature of about 20°-25° C. for 3 days, the mixture containing 5-formyl-2-aminothiazole hydrobromide was poured onto ice and neutralized with concentrated NH$_4$OH. The orange-red product, 5-formyl-2-aminothiazole, was collected by filtration, washed with cold water, and air dried to yield 77 g (0.6 m, 64%) of product. Additional product was obtained by concentrating the filtrates for a total yield of 106 g (0.83 m, 88%). The crude product was used for the preparation of the cyano compounds without further purification. The product can be recrystallized from hot water if desired to give gold needles, mp 165°–166.5° C. (uncorrected); see Vol. 12, p. 378, Journal of Medicinal Chemistry, giving mp of 160°–167° C. (melting with decomposition and resolidification after gradually darkening above 140° C.).

A typical preparation according to the present invention using the above unsubstituted intermediate is as follows:

Hydroxylamine hydrochloride (24.0 g, 0.30 m+15% molar excess), crude 2-amino-5-formylthiazole (38.4 g, 0.30 m), and sodium formate (37.5 g, 0.55 m) are combined in 450 ml of 97% (commercial) formic acid. The mixture is heated on a steam bath until TLC (10% $CH_3OH/CHCl_3$) shows only a single product spot (about 7–8 hr.). The reaction mixture is filtered hot and the filtrate condensed under reduced pressure. The residue is triturated in ice water, the solid collected by filtration, washed with water, and air-dried to yield 27.7 g (0.18 m, 60.5%) of 5-cyano-2-formamidothiazole as a reddish-brown powder.

The above formamide is refluxed on a steam bath in ethanolic HCl (42 ml of concentrated HCl and 280 ml ethanol, but this concentration can be widely varied as is known in the art) for 1½ hr. This time period also is not critical and can be widely varied by one skilled in the art. The reaction mixture is filtered hot and the filtrate concentrated to a slurry under reduced pressure. The slurry is added to about 200 ml of ice and water and neutralized with concentrated $NH_4OH$. The solid is collected by filtration, washed with water, and air-dried to give 19.7 g (0.16 m, 88%) of 2-amino-5-cyanothiazole. Recrystallization of the crude material from ethanol (charcoal) yields small reddish-brown crystals, mp 205.5°–207° C. (dec). The 4-substituted-2-amino-5-cyanothiazoles are prepared from the corresponding 4-substituted-2-amino-5-formylthiazoles by these procedures.

The novel compounds of the present invention include, for example, those of the formula

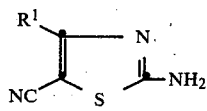

wherein $R^1$ is H, methyl, ethyl, propyl, octyl, n-butyl, methoxy, ethoxy, propoxy, butoxy, phenyl, o-chlorophenyl, o-bromophenyl, p-chlorophenyl, p-bromophenyl, 2-thiophene, α-pyridine, trifluoromethyl, and the like. The compounds and dyes therefrom which are most preferred are those wherein $R^1$ is H or phenyl.

A typical preparation of dyes from the present thiazoles is as follows:

Sodium nitrite (1.8 g, 0.025 m) is added portionwise with stirring to 13 ml of concentrated sulfuric acid below 80° C. The resulting nitrosylsulfuric acid solution is cooled, 25 ml of 1:5 acid (1 part propionic acid to 5 parts acetic acid) is added below 20° C., and 2-amino-5-cyanothiazole (3.1 g, 0.025 m) is added portionwise below 0° C., followed by 25 ml additional 1:5 acid below 0° C. After stirring for 2½ hrs. at about −5° to 2° C., the diazo solution is added slowly with stirring to an ice cold solution of N-cyanoethyl-N-ethylaniline (4.4 g, 0.025 m) in 125 ml. of 1:5 acid (couplers containing hydroxyl substituents were dissolved in 15% sulfuric acid). The resulting mixture is neutralized to Congo Red by the addition of solid ammonium acetate and allowed to stand at about 0° C. for 1 hr. The solid dye is precipitated with water, collected by filtration, washed with water until the filtrates are colorless, and air dried. The crude dye can be purified by slurrying in a hot solvent such as methanol, ethanol, or methyl cellosolve.

The invention has been described in detail with particular reference to certain preferred embodiments thereof, but it will be understood that variations and modifications can be effected within the spirit and scope of the invention.

I claim:

1. A compound of the formula

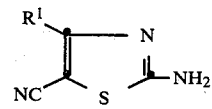

wherein $R^1$ is selected from hydrogen; straight or branched alkyl of 1–20 carbons which may be substituted with 1–3 halogens; phenyl and phenyl substituted with 1–3 halogens, straight or branched alkyl of 1–20 carbons, straight or branched alkoxy of 1–20 carbons, cyano, nitro or trifluoromethyl; 2-thiophene; and α-pyridine.

2. The compound according to claim 1 wherein $R^1$ is H.

3. The compound according to claim 1 wherein $R^1$ is phenyl.

4. The process for preparing the compounds of claim 1 comprising reacting in essentially anhydrous formic acid at from about 50° to about 110° C., hydroxylamine or a salt thereof, and the corresponding 2-amino-5-formylthiazole or a salt thereof, and hydrolyzing the intermediate 5-cyano-2-formamidothiazole to the amine.

5. The process of claim 4 wherein the reactions are carried out between about 85° C. and 105° C. and the hydrolysis reaction is carried out in ethanolic HCl.

6. The process of claim 4 wherein the mole ratio of the hydroxylamine or its salt to the corresponding 5-formyl-2-aminothiazole is from about 1:1 to about 2:1.

7. The process of claim 6 wherein sodium formate is present in the reaction of step one.

8. The process of claim 1 wherein the hydroxylamine salt is selected from $[NH_3OH]HSO_4$, $[NH_3OH]Cl$, $[NH_3OH]_2SO_4$, and $[NH_3OH]NO_3$.

9. The process of claim 1 wherein the hydroxylamine salt is $[NH_3OH]HSO_4$.

* * * * *